US010724065B2

United States Patent
Lee et al.

(10) Patent No.: US 10,724,065 B2
(45) Date of Patent: Jul. 28, 2020

(54) NOISE IMPROVEMENT IN DNA SEQUENCING CIRCUIT BY FINFET-LIKE NANOPORE FORMATION

(71) Applicant: QUALCOMM Incorporated, San Diego, CA (US)

(72) Inventors: Yong Ju Lee, San Diego, CA (US); Joung Won Park, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 86 days.

(21) Appl. No.: 15/438,734

(22) Filed: Feb. 21, 2017

(65) Prior Publication Data

US 2018/0238824 A1    Aug. 23, 2018

(51) Int. Cl.
*H01L 29/417* (2006.01)
*C12Q 1/00* (2006.01)
(Continued)

(52) U.S. Cl.
CPC ........... *C12Q 1/002* (2013.01); *C12Q 1/6874* (2013.01); *G01N 27/4145* (2013.01);
(Continued)

(58) Field of Classification Search
CPC ......... G01N 27/3275; G01N 33/48721; G01N 27/414; G01N 27/4075; C12Q 1/002; C12Q 1/6874; C12Q 2565/607
See application file for complete search history.

(56) References Cited

U.S. PATENT DOCUMENTS 8,535,512 B2    9/2013    Walavalkar et al.
8,652,340 B2    2/2014    Stolovitzky et al.
(Continued)

FOREIGN PATENT DOCUMENTS

WO    02054450 A2    7/2002
WO    2015127387 A1    8/2015

OTHER PUBLICATIONS

Balan A., et al., "Improving Signal-to-Noise Performance for DNA Translocation in Solid-State Nanopores at MHz Bandwidths", NANO Letters, vol. 14, No. 12, Dec. 10, 2014, pp. 7215-7220, XP055467127, ISSN: 1530-6984, DOI: 10.1021/nl504345y.
(Continued)

*Primary Examiner* — Steven H Loke
*Assistant Examiner* — Samuel Park
(74) *Attorney, Agent, or Firm* — Muncy, Geissler, Olds & Lowe, P.C./QUALCOMM

(57) ABSTRACT

The disclosure generally relates to a deoxyribonucleic acid (DNA) sequencing circuit having a controllable pore size and a lower membrane capacitance and noise floor relative to biological nanopore devices. For example, design principles used to fabricate a fin-shaped field effect transistor (FinFET) may be applied to form, on a first wafer, a nanopore that has a desired pore size in a silicon-based membrane. Electrodes and an interconnect embedded with an amplifier and analog-to-digital converter (ADC) may be formed on a separate second wafer, wherein the first wafer and the second wafer may then be bonded and further processed to form a sensing device that includes appropriate wells and pores to be used in a DNA sequencing circuit.

9 Claims, 11 Drawing Sheets

(51) Int. Cl.
*C12Q 1/6874* (2018.01)
*G01N 27/414* (2006.01)
*G01N 33/487* (2006.01)
*C12Q 1/6869* (2018.01)

(52) U.S. Cl.
CPC ..... *C12Q 1/6869* (2013.01); *C12Q 2565/607* (2013.01); *G01N 33/48721* (2013.01)

(56) References Cited

U.S. PATENT DOCUMENTS

| | | | |
|---|---|---|---|
| 9,034,637 B2 | 5/2015 | Merz et al. | |
| 2003/0003609 A1 | 1/2003 | Sauer et al. | |
| 2011/0105366 A1* | 5/2011 | Lebl | B01J 19/0046 |
| | | | 506/32 |
| 2011/0133255 A1* | 6/2011 | Merz | G01N 33/48721 |
| | | | 257/253 |
| 2011/0279125 A1* | 11/2011 | Bedell | B82Y 15/00 |
| | | | 324/444 |
| 2013/0069665 A1 | 3/2013 | Jaramillo-Botero et al. | |
| 2013/0109577 A1* | 5/2013 | Korlach | G01N 27/3278 |
| | | | 506/4 |
| 2013/0291627 A1 | 11/2013 | Hu et al. | |
| 2013/0327645 A1 | 12/2013 | Walavalkar et al. | |
| 2014/0004300 A1 | 1/2014 | Bai et al. | |
| 2016/0178569 A1* | 6/2016 | Hoffman | G01N 27/4146 |
| | | | 257/29 |
| 2017/0059514 A1* | 3/2017 | Hoffman | G01N 27/4146 |
| 2017/0097332 A1* | 4/2017 | Paik | C12Q 1/6869 |

OTHER PUBLICATIONS

International Search Report and Written Opinion—PCT/US2018/012057—ISA/EPO—dated Apr. 24, 2018.

* cited by examiner

US 10,724,065 B2

NOISE IMPROVEMENT IN DNA SEQUENCING CIRCUIT BY FINFET-LIKE NANOPORE FORMATION

TECHNICAL FIELD

The various aspects and embodiments described herein generally relate to a deoxyribonucleic acid (DNA) sequencing circuit having a controllable pore size and a lower membrane capacitance and noise floor relative to biological nanopore devices.

BACKGROUND

Deoxyribonucleic acid (DNA), sometimes called the "blueprint of life", is a molecule that stores biological information. DNA has a basic structure that consists of two biopolymer strands, which are coiled around one another to form a double helix. Each strand is a polynucleotide that includes various nucleotides, which include cytosine ("C"), guanine ("G"), adenine ("A"), and thymine ("T"). Each nucleotide in one DNA strand may be bonded to a paired nucleotide in the other strand, thereby forming a base pair. Generally, cytosine and guanine are paired to form a "G-C" or "C-G" base pair, and adenine and thymine are paired to form an "A-T" or "T-A" base pair. Although the structure of DNA is now known, new methods to analyze individual DNA molecules are still being developed. Generally, the analysis includes "reading" the nucleotide sequence of a particular DNA strand. In one method, known as nanopore DNA sequencing, a nanopore is immersed in a conductive fluid, and a voltage is applied across the nanopore. As a result, ions are conducted through the nanopore, thereby generating a measurable electric current. A DNA strand is then transmitted through a nanopore, one nucleotide at a time. The presence of a nucleotide within the nanopore disrupts the conduction of the ions, thereby causing a change in the electric current. Moreover, the change in electrical current due to a particular nucleotide differs from the change in electrical current due to other nucleotides. Accordingly, an entire DNA strand can be transmitted through the nanopore and each nucleotide in the strand can be identified based on the change in current. Over time, the changes in electric current result in a DNA sensing signal reflecting the nucleotide sequence in a DNA strand.

As nanopore DNA sequencing improves, new challenges are presented. For example, although biological nanopores have shown promising experimental results to sequence single-stranded DNA (ssDNA), these protein pores have a constant pore size and lack stability. In addition, biological nanopores suffer from the fragility of traditional supported lipid membranes and a high membrane capacitance (~50 femtofarads). The membrane capacitance may reduce the maximum cutoff frequency and thus limit the bandwidth associated with the DNA sensing signal in addition to increasing a noise component. As a result, new technologies are needed to further improve nanopore-based DNA sensing devices.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

According to various aspects, mechanisms to form a fin-shaped field effect transistor (FinFET) may be applied to form a deoxyribonucleic acid (DNA) sequencing circuit with a silicon-based nanopore that has a controllable (i.e., variable) pore size and a lower membrane capacitance and a lower noise floor compared to biological nanopore devices. For example, a silicon (Si) fin may be formed on a silicon on insulator (SOI) wafer, wherein the Si fin may have a controllable width. Silicon dioxide ($SiO_2$) may then be grown over the Si fin, a chemical mechanical polishing (CMP) process may be performed to planarize a surface of the Si fin and the $SiO_2$ layer, and a wet etching process may be performed to remove (e.g., dissolve) the Si fin. The original Si fin shape may thereby form a FinFET-like nanopore with a controllable pore size. Electrodes and an interconnect embedded with an amplifier and analog-to-digital converter (ADC) may be formed on a separate second wafer. The SOI wafer and the second wafer may then be bonded to form a sensing device that includes wells and pores, wherein the sensing device may be used in a DNA sequencing circuit. Experimental simulation results show that the fabrication methods to be described in further detail herein substantially reduce membrane capacitance and a noise floor compared to biological nanopore devices.

Other objects and advantages associated with the aspects and embodiments disclosed herein will be apparent to those skilled in the art based on the accompanying drawings and detailed description.

BRIEF DESCRIPTION OF THE DRAWINGS

A more complete appreciation of the various aspects and embodiments described herein and many attendant advantages thereof will be readily obtained as the same becomes better understood by reference to the following detailed description when considered in connection with the accompanying drawings which are presented solely for illustration and not limitation, and in which.

DETAILED DESCRIPTION

Various aspects and embodiments are disclosed in the following description and related drawings to show specific examples relating to exemplary aspects and embodiments. Alternate aspects and embodiments will be apparent to those skilled in the pertinent art upon reading this disclosure, and may be constructed and practiced without departing from the scope or spirit of the disclosure. Additionally, well-known elements will not be described in detail or may be omitted so as to not obscure the relevant details of the aspects and embodiments disclosed herein.

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments include the discussed feature, advantage, or mode of operation.

The terminology used herein describes particular embodiments only and should not be construed to limit any embodiments disclosed herein. As used herein, the singular forms "a," "an," and "the" are intended to include the plural forms as well, unless the context clearly indicates otherwise. Those skilled in the art will further understand that the terms "comprises," "comprising," "includes," and/or "including," as used herein, specify the presence of stated features, integers, steps, operations, elements, and/or components, but do not preclude the presence or addition of one or more other features, integers, steps, operations, elements, components, and/or groups thereof.

Further, various aspects and/or embodiments may be described in terms of sequences of actions to be performed by, for example, elements of a computing device. Those skilled in the art will recognize that various actions described herein can be performed by specific circuits (e.g., an application specific integrated circuit (ASIC)), by program instructions being executed by one or more processors, or by a combination of both. Additionally, these sequence of actions described herein can be considered to be embodied entirely within any form of non-transitory computer-readable medium having stored thereon a corresponding set of computer instructions that upon execution would cause an associated processor to perform the functionality described herein. Thus, the various aspects described herein may be embodied in a number of different forms, all of which have been contemplated to be within the scope of the claimed subject matter. In addition, for each of the aspects described herein, the corresponding form of any such aspects may be described herein as, for example, "logic configured to" and/or other structural components configured to perform the described action.

Figure 1:
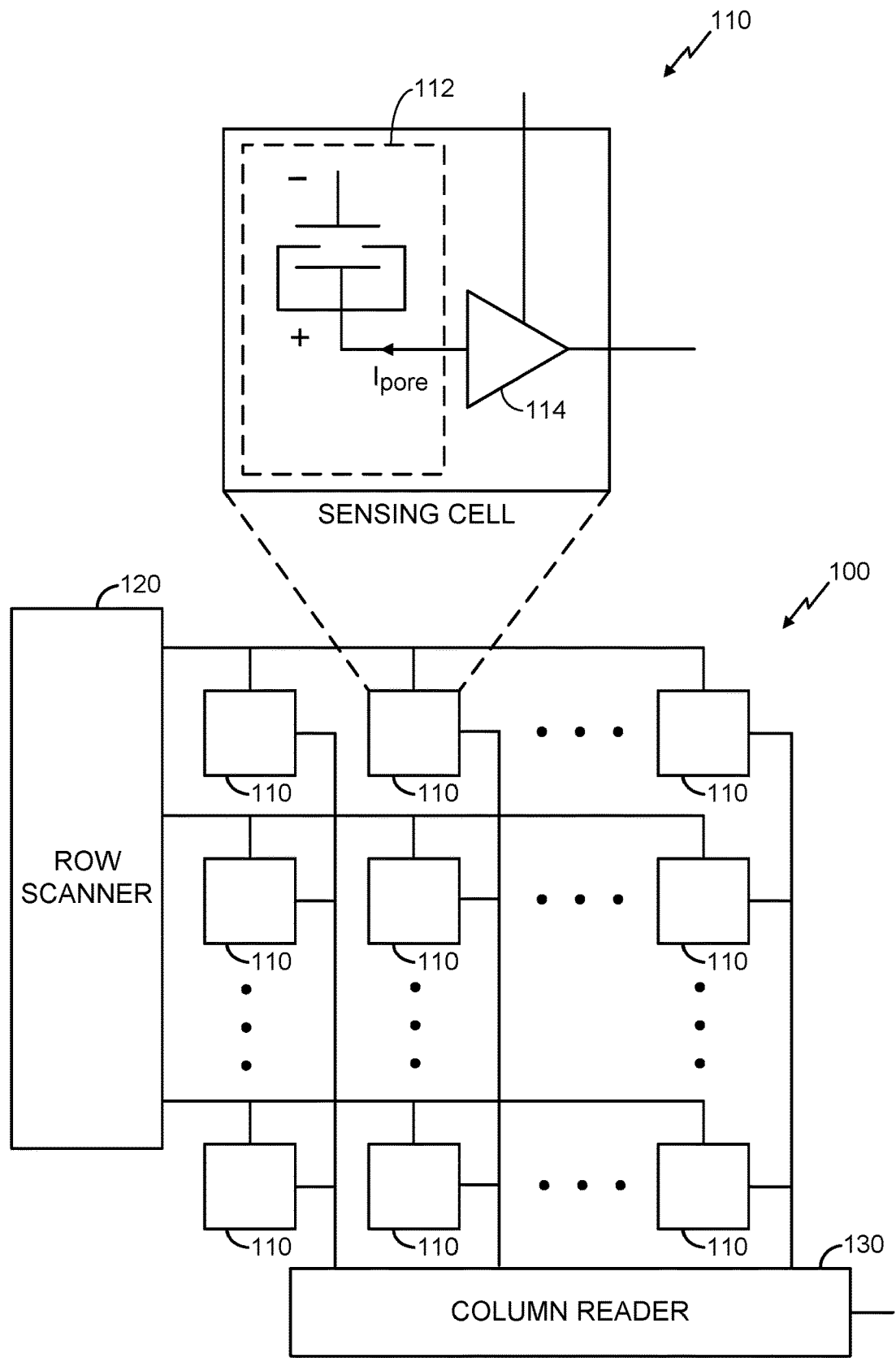
FIG. 1 illustrates an example DNA sensor array that includes various sensing cells, according to various aspects.

According to various aspects, FIG. 1 illustrates an example DNA sensor array 100 that includes various sensing cells 110. As shown in FIG. 1, the various DNA sensing cells 110 may be arranged in rows and columns to form a grid pattern. The DNA sensor array 100 may further include a row scanner 120 and a column reader 130. The row scanner 120 and column reader 130 may facilitate reading a particular DNA sensing cell 110 from among the various DNA sensing cells 110. Each DNA sensing cell 110 may include a DNA sensing device 112 and an amplifier 114. As will be described in further detail below, the DNA sensing device 112 may dynamically generate an electric current as a DNA strand is transmitted through a nanopore in the DNA sensing device 112. Over time, the changes in electric current result in a DNA sensing signal reflecting the particular nucleotide sequence in a particular DNA strand, wherein the amplifier 114 may generally amplify the DNA sensing signal.

Figure 2:
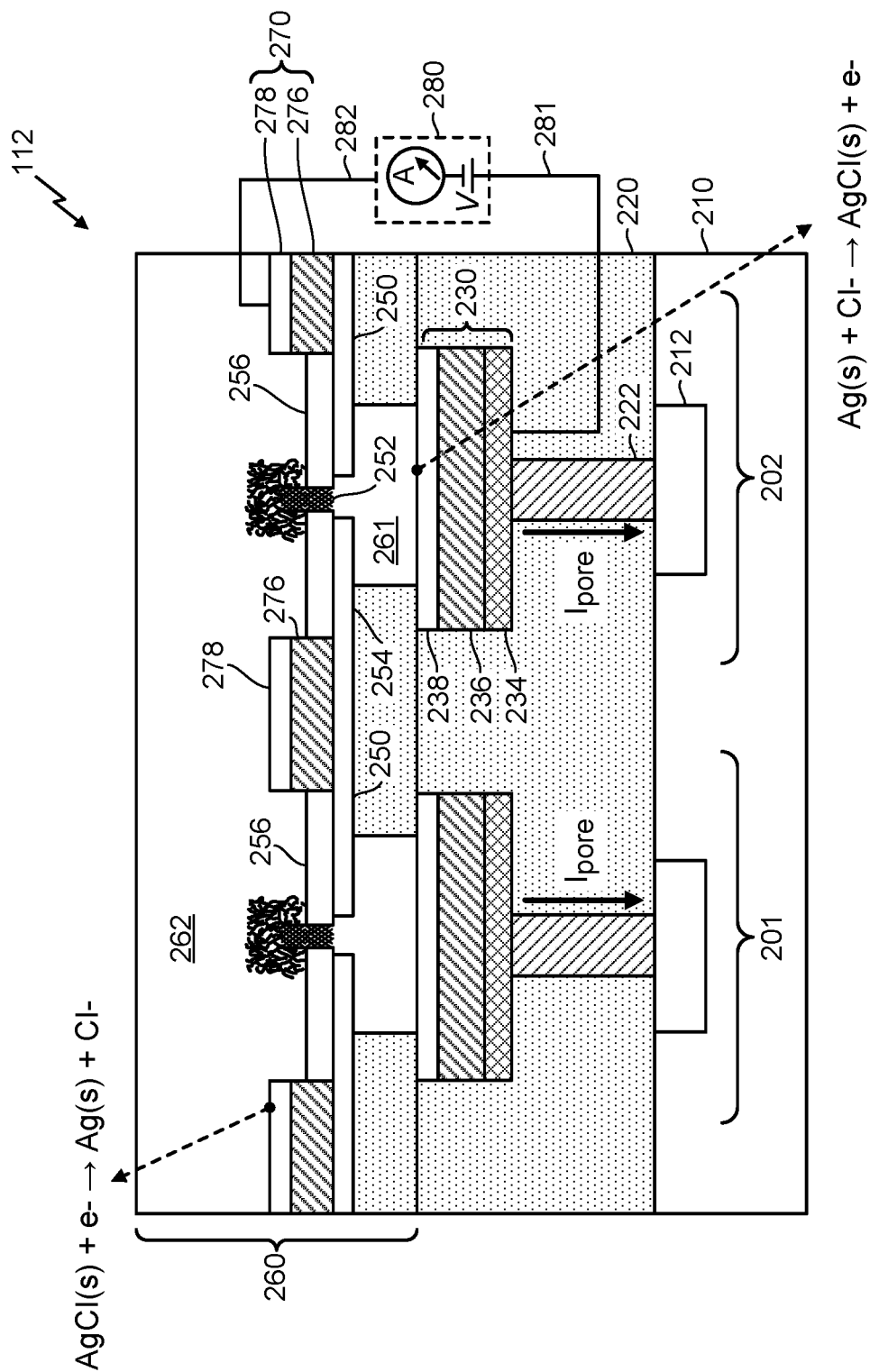
FIG. 2 illustrates an example nanopore-based DNA sensing device that can be used in a sensing cell as shown in FIG. 1, according to various aspects.

According to various aspects, FIG. 2 illustrates an example nanopore-based DNA sensing device 112 that can be used in the various DNA sensing cells 110 within the DNA sensor array 100 as shown in FIG. 1. The nanopore-based DNA sensing device 112 may generally include a pair of nanopore-based DNA sensing devices 201, 202 formed on a substrate 210 and at least partially within an insulator 220. For example, in various embodiments, the substrate 210 may comprise silicon (Si) and the insulator 220 may comprise silicon oxide ($SiO_2$), silicon mononitride (SiN), a hydrophilic material, and/or other suitable material(s) and/or combinations thereof. The DNA sensing devices 201, 202 may be disposed in adjacent DNA sensing cells analogous to the DNA sensing cells 110 depicted in FIG. 1. Furthermore, the DNA sensing devices 201, 202 depicted in FIG. 2 may be substantially similar to one another. Accordingly, in the following description, the particular components of the nanopore-based DNA sensing devices 201, 202 will be described with reference to nanopore-based DNA sensing device 202 only for clarity.

The DNA sensing device 202 may include a semiconductor device 212 disposed on the substrate 210. The semiconductor device 212 may include, for example, a complementary metal oxide semiconductor (CMOS) transistor. The semiconductor device 212 may be a component of an amplifier analogous to the amplifier 114 depicted in FIG. 1. The insulator 220 may include a via 222 in contact with the semiconductor device 212. The via 222 may include, for example, copper (Cu), tungsten (W), aluminum (Al), any combination thereof, and/or any other suitable material(s).

The DNA sensing device 202 may further include a first electrode 230 in contact with the via 222. The first electrode 230 may be disposed on or within the insulator 220. The first electrode 230 may include an adhesion/diffusion layer 234, a conductive layer 236, and a surface layer 238. For example, the adhesion/diffusion layer 234 may include a chromium (Cr) adhesion layer in contact with the via 222 and a gold (Au) diffusion layer between the conductive layer 236 and the Cr adhesion layer. Alternatively and/or additionally, the adhesion/diffusion layer 234 may include titanium nitride (TiN) and/or any other suitable material(s). The conductive layer 236 may include silver (Ag) and the surface layer 238 may include silver chloride (AgCl). However, those skilled in the art will appreciate that any other suitable material(s) may be selected.

The DNA sensing device 202 further includes a separation layer 250 having a nanopore 252 embedded therein. The separation layer 250 may include a barrier layer 254 and a hydrophobic layer 256. The barrier layer 254 may include silicon nitride ($Si_3N_4$) and/or other suitable material(s). The hydrophobic layer 256 may include a lipid bilayer (LBL) membrane, a hydrophobic membrane, or any other suitable material(s).

The DNA sensing device 202 further includes a chamber 260, which may hold a conductive fluid. For example, in various embodiments, the conductive fluid may include an electrolyte such as potassium chloride solvated into potassium ions (K+) and chlorine ions (Cr). However, those skilled in the art will appreciate that the conductive fluid may comprise other suitable electrolyte(s). In various embodiments, the separation layer 250 or a component thereof (e.g., the barrier layer 254 and the hydrophobic layer 256) may divide the conductive fluid within the chamber 260 into a first sub-chamber 261 and a second sub-chamber 262.

The DNA sensing device 202 may further include a second electrode 270 disposed on the separation layer 250. The second electrode 270 may include a conductive layer 276 and a surface layer 278, which may be analogous to the conductive layer 236 and the surface layer 238 of the first electrode 230. The first electrode 230 may be coupled to a voltage source 280 via a first conductor 281 and the second electrode 270 may be coupled to the voltage source 280 via a second conductor 282.

Fluid in the first sub-chamber 261 may be in contact with the surface layer 238 of the first electrode 230, and fluid in the second sub-chamber 262 may be in contact with the surface layer 278 of the second electrode 270. In the DNA sensing device 202 as shown in FIG. 2, the first sub-chamber 261 may be a positive chamber (i.e., associated with a trans-electrode) and the second sub-chamber 262 may be a negative chamber (i.e., associated with a cis-electrode). However, those skilled in the art will appreciate that the polarity associated with sub-chambers 261, 262 may be reversed.

Although the chamber 260 is depicted as a closed chamber, those skilled in the art will appreciate that the chamber 260 may instead be an open chamber. Moreover, as will be discussed in greater detail below, the chamber 260 may include enough conductive fluid to fill the first sub-chamber 261 and cover the second electrode 270.

Figure 3:
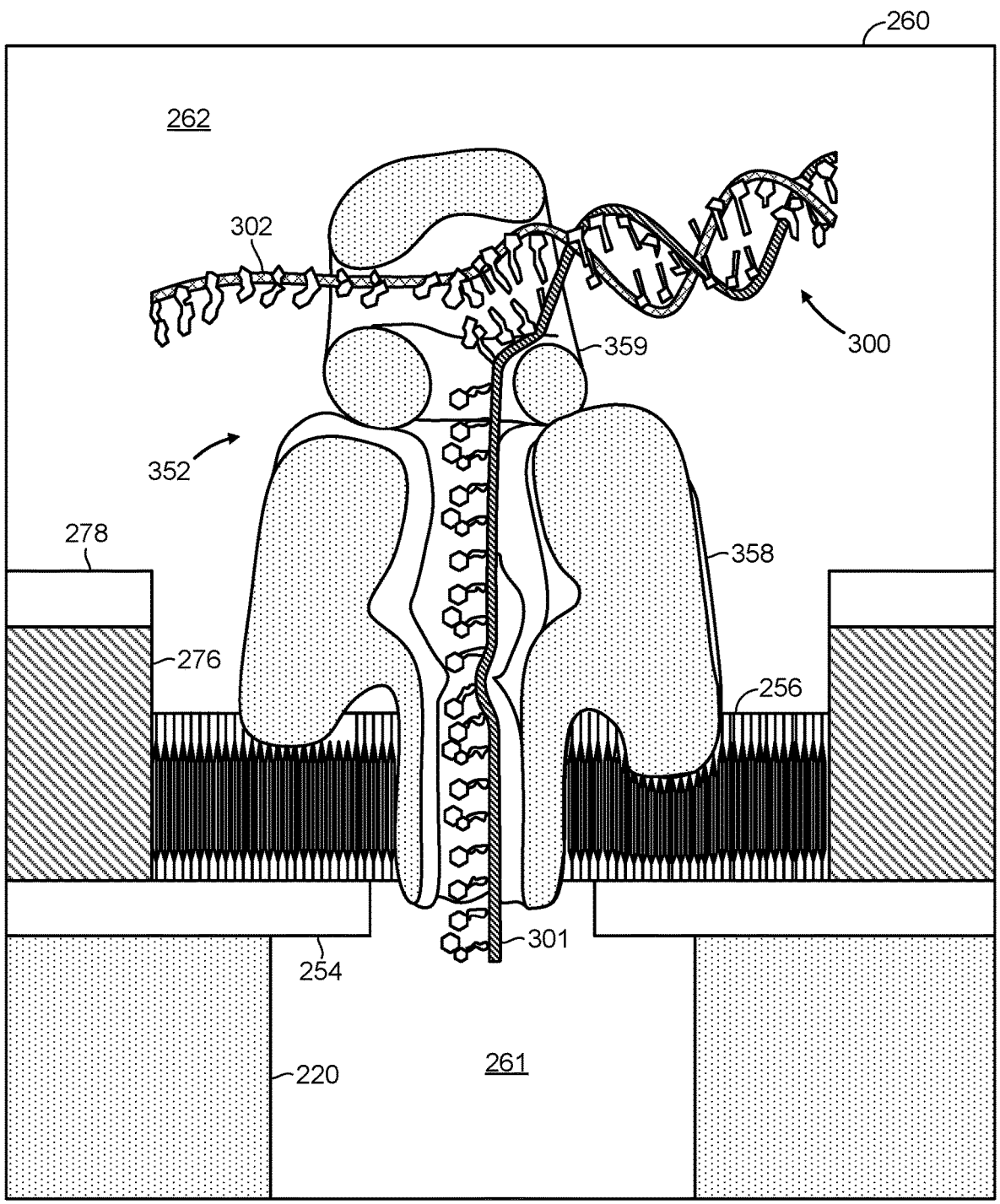
FIG. 3 illustrates the separation and/or combination of a double-stranded DNA molecule in a nanopore-based DNA sensing device, according to various aspects.

According to various aspects, FIG. 3 generally illustrates a nanopore 352, which may be used as the nanopore 252 in the DNA sensing device 112 shown in FIG. 1 and FIG. 2. In the example shown in FIG. 3, the nanopore 352 is a biological nanopore providing a protein channel in a high electrical resistance lipid bilayer. However, the term "nanopore" simply means a small hole with an internal diameter around one nanometer (~1 nm). As such, while the nanopore 352 illustrated in FIG. 3 is a biological nanopore (e.g., a hollow core passing through a mushroom-shaped protein molecule), those skilled in the art will appreciate that the nanopore 352 could be a solid-state nanopore formed as a hole in a synthetic material (e.g., a silicon or graphene-based membrane), a hybrid biological-synthetic nanopore (e.g., a protein channel set in a synthetic membrane), etc. Furthermore, as will be described in further detail below, the various aspects and embodiments described herein contemplate that the nanopore 352 may be a silicon-based nanopore created using design principles associated with a fin-shaped field effect transistor (FinFET).

As noted above, when used as the nanopore 252 in the DNA sensing device 112 shown in FIG. 1 and FIG. 2, the nanopore 352 may be embedded in the separation layer 250, which may separate the first sub-chamber 261 from the second sub-chamber 262. As noted previously, the separation layer 250 may include a lipid bilayer (LBL) membrane, a hydrophobic membrane, or any other suitable material(s). Referring specifically to FIG. 3, the nanopore 352 may include a translocator 358 and an assembler 359. The translocator 358 permits fluid communication (e.g., passage of conductive fluid) between the first sub-chamber 261 and the second sub-chamber 262. For example, if the second sub-chamber 262 is negatively charged and the first sub-chamber 261 is positively charged, then negative ions (e.g., Cr) may pass from the second sub-chamber 262 to the first sub-chamber 261 via the translocator 358 and/or positive ions (e.g., $K^+$ and/or $H^+$) may pass from the first sub-chamber 261 to the second sub-chamber 262. In various embodiments, the translocator 358 may include alpha hemolysin or another suitable pore-forming protein (e.g., Mycobacterial (MspA) porin). The assembler 359 may separate a double-stranded DNA molecule 300 into a first single-stranded DNA (ssDNA) strand 301 and a second ssDNA strand 302. Alternatively and/or additionally, the assembler 359 may combine the first ssDNA strand 301 and the second ssDNA strand 302 into the double-stranded DNA molecule 300. In some implementations, the assembler 359 may include DNA polymerase.

According to various aspects, FIG. 3 further illustrates the manner in which the double-stranded DNA molecule 300 may be separated into the first and second ssDNA strands 301, 302 and/or formed from combining the first and second ssDNA strands 301, 302 when passed through the nanopore 352. For example, the double-stranded DNA molecule 300 may move from the second sub-chamber 262 into the assembler 359, where the double-stranded DNA molecule 300 is separated into the first and second ssDNA strands 301, 302. The first ssDNA strand 301 may be led into the translocator 358 and translocated across the hydrophobic layer 256 and the barrier layer 254 that together form the separation layer 250, thereby passing from the second sub-chamber 262 into the first sub-chamber 261. In another example, the first ssDNA strand 301 may be drawn from the first sub-chamber 261 through the translocator 358 and into the assembler 359, where the first ssDNA strand 301 is combined with the second ssDNA strand 302 into the double-stranded DNA molecule 300. The double-stranded DNA molecule 300 may then move into the second sub-chamber 262.

According to various aspects, referring again now to FIG. 2, the following method may be used to perform DNA sequencing using the DNA sensing device 202 based on the functional properties associated with the nanopore 352 of as shown in FIG. 3 and described in further detail above. For example, in various embodiments, a voltage may initially be applied to the first electrode 230 via the first conductor 281 and to the second electrode 270 via the second conductor 282. As a result, a positive charge may appear on the first electrode 230 and a negative charge may appear on the second electrode 270. In one example, the surface layer 278 associated with the second electrode 270 may comprise silver chloride (AgCl) and the conductive layer 276 may comprise silver (Ag). When the voltage is applied such that the negative charge appears on the second electrode 270, the solid AgCl in the surface layer 278 may be converted into Ag and negatively charged chlorine (Cl) ions, i.e., $AgCl(s) + e^- \rightarrow Ag(s) + Cl^-$. As the second electrode 270 generates the $Cl^-$ ions, which mix with the electrolyte held in the second sub-chamber 262, the second sub-chamber 262 becomes negatively charged.

Moreover, the surface layer 238 and the conductive layer 236 associated with the first electrode 230 may likewise comprise silver chloride (AgCl) and silver (Ag), respectively. As such, when the voltage is applied such that the positive charge appears on the first electrode 230, the solid Ag in the conductive layer 236 may react with the $Cl^-$ ions in the first sub-chamber 261 to yield solid AgCl and negatively charged electrons, i.e., Ag(s)+Cl⁻→AgCl(s)+e⁻. As the first electrode 230 combines the solid silver with the Cl⁻ ions in the first sub-chamber 261 to produce solid AgCl, the first sub-chamber 261 has more positively charged ions compared to negatively charged ions, whereby the first sub-chamber 261 becomes positively charged. As a result, ions in the chamber 260 may have a tendency to flow toward either the first sub-chamber 261 (which is positively charged) or the second sub-chamber 262 (which is negatively charged). For example, Cl⁻ ions in the chamber 260, which include the Cl⁻ ions generated at the second electrode 270, may tend to flow from the negatively charged second sub-chamber 262 toward the positively charged first sub-chamber 261.

According to various aspects, as the first electrode 230 generates negatively charged electrons e⁻, an electrical current $I_{PORE}$ may flow through the via 222 to the semiconductor device 212. Because Cl⁻ ions may tend to flow toward the positively charged first sub-chamber 261, the Cl⁻ ions may translocate across the separation layer 250 via the nanopore 252. However, the nanopore 252 may also be configured to translocate DNA (e.g., the first ssDNA strand 301 as shown in FIG. 3). For example, as the first ssDNA strand 301 translocates across the separation layer 250 via the nanopore 252, the first ssDNA strand 301 may impede the flow of Cl⁻ ions through the nanopore 252. As a result, the electrical current $I_{PORE}$ may be reduced due to the translocated first ssDNA strand 301. Moreover, different nucleotides may have different effects on the flow of Cl⁻ ions through the nanopore 252. Accordingly, as different nucleotides pass through the nanopore 252, different quantities of Cl⁻ ions may pass through the nanopore 252 and a different electrical current $I_{PORE}$ may be measured at the semiconductor device 212. For example, a cytosine (C) nucleotide may cause an electrical current $I_C$ to be measured at the semiconductor device 212, a guanine (G) nucleotide may cause an electrical current $I_G$ to be measured at the semiconductor device 212, an adenine (A) nucleotide may cause an electrical current $I_A$ to be measured at the semiconductor device 212, and a thymine (T) nucleotide may cause an electrical current $I_T$ to be measured at the semiconductor device 212, wherein $I_C$, $I_G$, $I_A$, and $I_T$ may each have different values. Accordingly, as the first ssDNA strand 301 passes through the nanopore 252, the DNA sensing device 202 may generate a current waveform $I_{PORE}(t)$ that indicates the electrical current measured at the semiconductor device 212 over time and thus the nucleotide sequence in the first ssDNA strand 301

Figure 4:
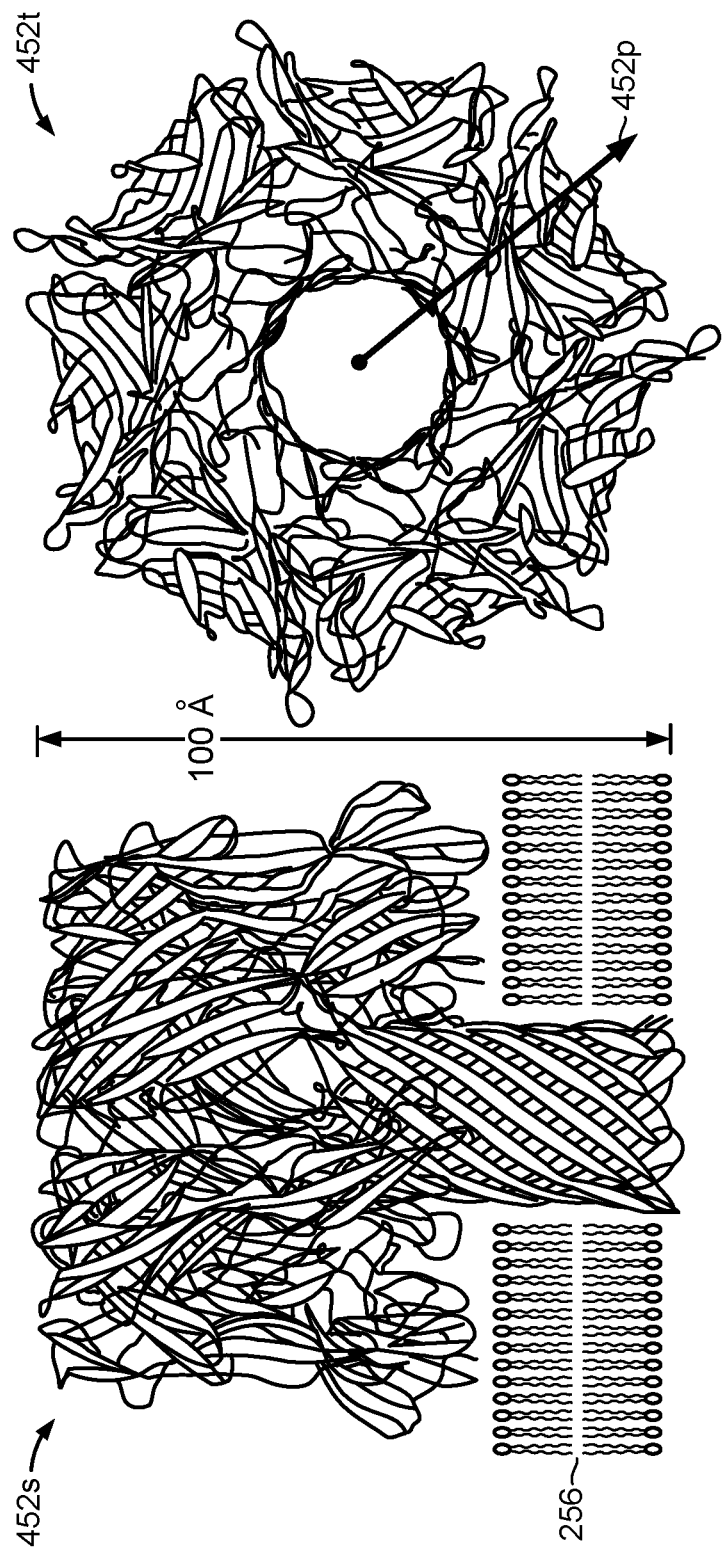
FIG. 4 illustrates an example biological nanopore, according to various aspects.

Biological nanopores such as the nanopore 352 shown in FIG. 3 have shown promising experimental results in providing the ability to sequence single-stranded DNA (ssDNA). However, biological nanopores present various challenges and drawbacks. For example, FIG. 4 illustrates a biological nanopore formed in an alpha hemolysin (alpha-HL) protein according to a side view 452s and a top view 452t. As shown in FIG. 4, the alpha-HL protein is a mushroom-shaped protein molecule with an approximately one-hundred Angstrom (100A) height and diameter. However, because the alpha-HL protein is a biological molecule, the resultant biological nanopore 452p has a constant pore size (i.e., approximately 1.4 nm), and the same issues with respect to constant pore size apply to biological nanopores created in other pore-forming proteins (e.g., Mycobacterial (MspA) porin has a 1.2 nm pore size). In addition, biological nanopores tend to lack stability and suffer from fragility associated with the supported lipid membrane 256, which may cause significant noise due to membrane capacitance ($C_{memb}$) approaching fifty femtofarads (~50 fF) at 10 KHz. Accordingly, the following description details an approach to control pore sizes in a DNA sensing device having a mechanically robust membrane and a low membrane capacitance.

Figure 5:
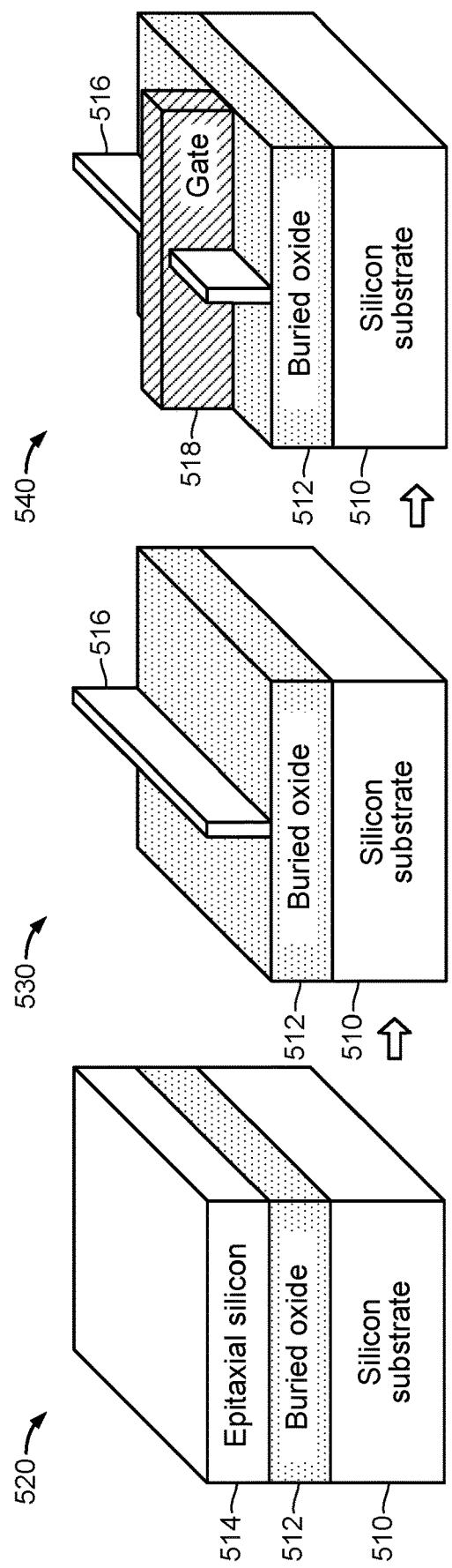
FIG. 5 illustrates an exemplary process flow to form a silicon-on-insulator (SOI) fin-shaped field-effect transistor (FinFET), according to various aspects.

More particularly, according to various aspects, FIG. 5 illustrates an exemplary process flow to form a silicon-on-insulator (SOI) fin-shaped field-effect transistor (FinFET), wherein such mechanisms may be used to form silicon-based nanopores with a controlled pore size and improve performance in a DNA sequencing circuit. For example, as depicted at 520, an oxide layer 512 (e.g., a silicon dioxide ($SiO_2$) layer) may be formed on a silicon (Si) substrate 510 and an epitaxial silicon Si layer 514 may be formed on the oxide layer 512. The epitaxial silicon Si layer 514 may then be etched or otherwise processed such that only a silicon fin 516 remains, as depicted at 530. Accordingly, a gate structure 518 is then formed around the silicon fin 516 in a channel region, forming the FinFET with source, channel, and drain regions as depicted at 540.

Figure 6A:
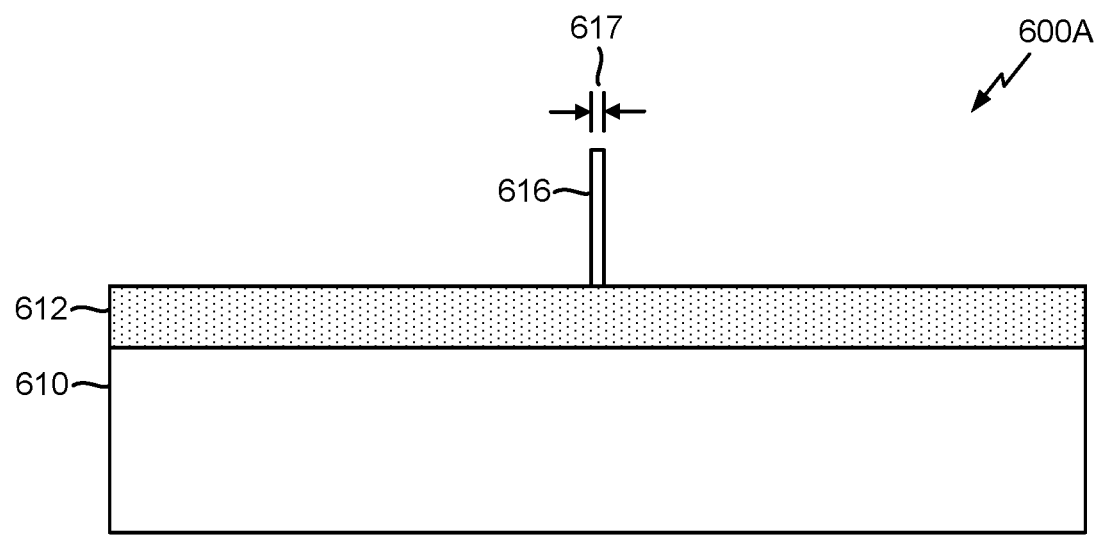
FIG. 6A-6D illustrate an exemplary process flow to form a FinFET-like nanopore on a silicon-on-insulator (SOI) wafer, according to various aspects.
Figure 6B:
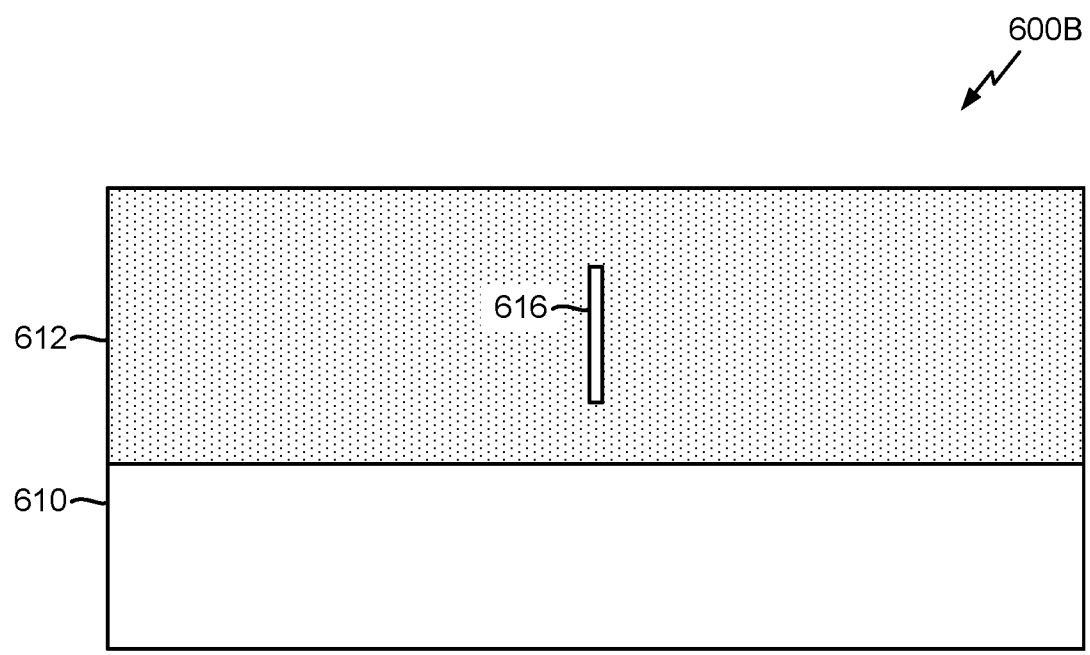
Figure 6C:
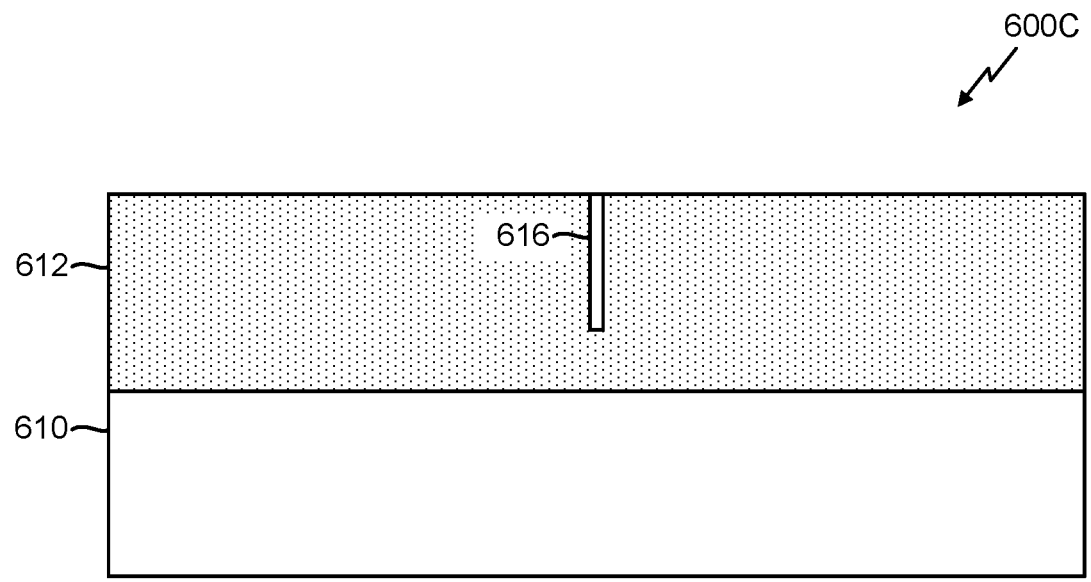

According to various aspects, 6A-6D illustrate an exemplary process flow to form a FinFET-like nanopore on a silicon-on-insulator (SOI) wafer based on the above-mentioned design principles. For example, FIG. 6A illustrates a starting structure 600A that may be substantially similar to the structure 530 as shown in FIG. 5. In particular, the starting structure 600A comprises a silicon (Si) substrate 610, a silicon dioxide ($SiO_2$) layer 612 formed on the Si substrate 610, and an Si fin 616 formed on the $SiO_2$ layer 612. In various embodiments, the Si fin 616 may have a width 617 in a range from approximately one nanometer (1 nm) to one micrometer (1 μm), wherein the width 617 associated with the Si fin 616 may correspond to a desired pore size associated with an Si-based nanopore to be used in a DNA sequencing circuit. Referring to FIG. 6B, the $SiO_2$ layer 612 may then be grown such that the Si fin 616 is buried therein, resulting in the structure 600B. The $SiO_2$ layer 612 and the buried Si fin 616 may then be planarized through chemical mechanical polishing (CMP), resulting in the structure 600C shown in FIG. 6C. The Si fin 616 may then be removed, for example, dissolved via wet etching in hydrofluoric (HF) acid, resulting in the structure 600D shown in FIG. 6D where the Si fin 616 has been removed to create a FinFET-like nanopore 618 having a width 619, which may be substantially equivalent to the width 617 of the Si fin 616.

According to various aspects, 7A-7B illustrate an exemplary process flow to embed electrodes and an interconnect with an amplifier and analog-to-digital converter (ADC) on a silicon-on-insulator (SOI) wafer. The process flow shown in FIG. 6A-6D may be performed on a first SOI wafer and the process flow shown in FIG. 7A-7B may be performed on a (separate) second SOI wafer. For example, FIG. 7A illustrates a starting structure 700A in which the amplifier and the ADC form a first layer 710, a silicon (Si) substrate 712 is disposed above the amplifier/ADC layer 710, and a silicon dioxide ($SiO_2$) layer 714 is formed on the Si substrate 712. Referring to FIG. 7B, an opening 720 may be formed in the $SiO_2$ layer 714 and the Si substrate 712, wherein a first electrode 718 and a first interconnect 716 may be formed in the opening 720, resulting in the structure depicted at 700B. For example, in various embodiments, the first electrode 718 may be formed from silver (Ag) and the first interconnect 716 may be formed from copper (Cu). However, those skilled in the art will appreciate that the first electrode 718 and/or the first interconnect 716 may be other suitable material(s).

Figure 6D:
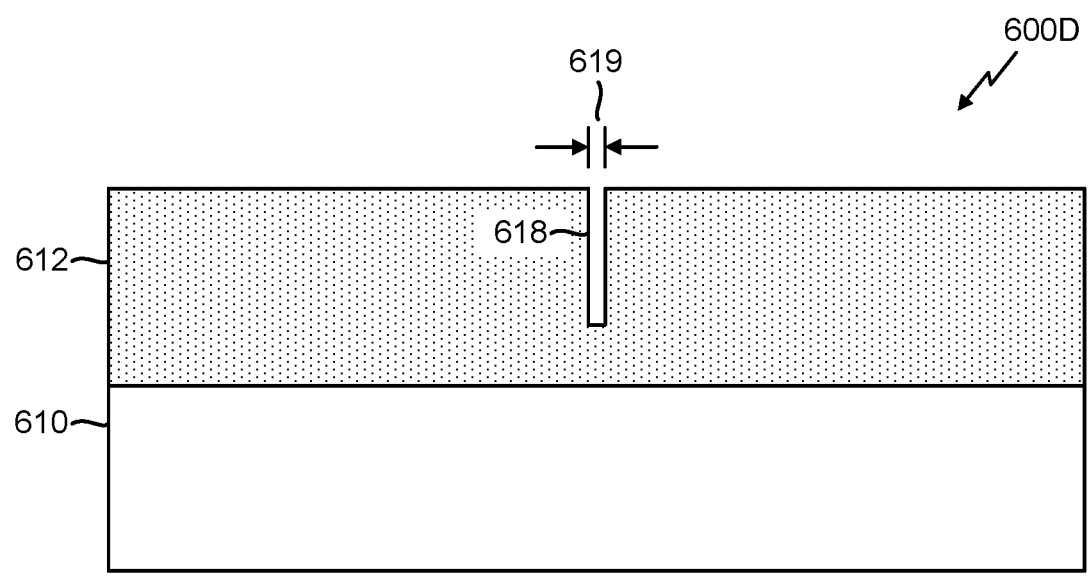
Figure 7A:
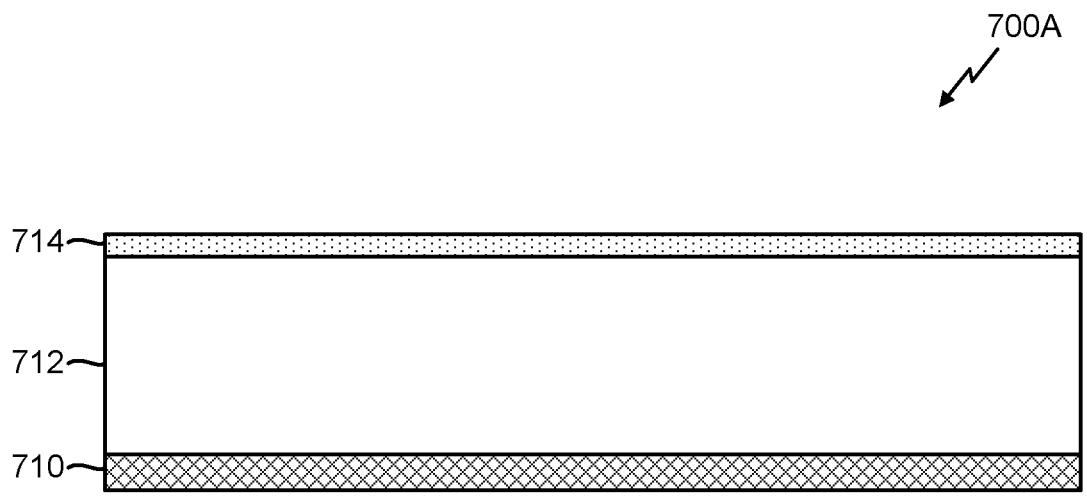
FIG. 7A-7B illustrate an exemplary process flow to embed electrodes and an interconnect with an amplifier and analog-to-digital converter (ADC) on a silicon-on-insulator (SOI) wafer, according to various aspects.
Figure 7B:
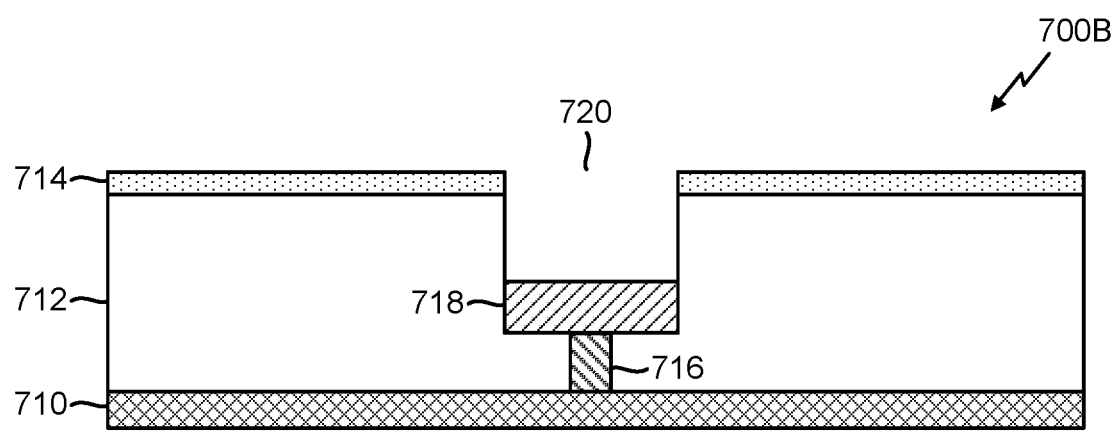
Figure 8:
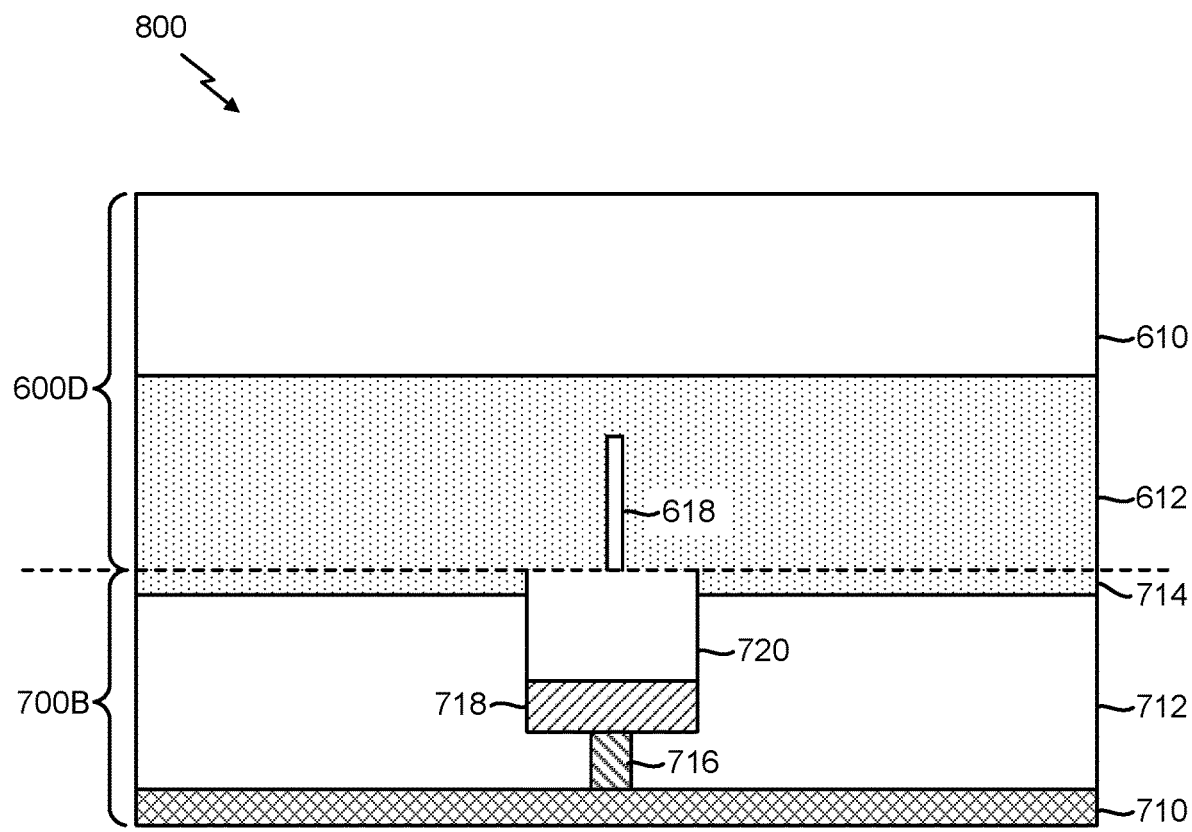
FIG. 8 illustrates an exemplary structure in which a first SOI wafer having a FinFET-like nanopore is bonded to a second SOI wafer having electrodes and an interconnect embedded with an amplifier and ADC, according to various aspects.

According to various aspects, FIG. 8 illustrates an exemplary structure 800 in which the structure 600D as shown in FIG. 6D is bonded to the structure 700B as shown in FIG. 7B. In particular, FIG. 8 illustrates an $SiO_2$-to-$SiO_2$ bonding between the $SiO_2$ layer 612 in the structure 600D and the $SiO_2$ layer 714 in the structure 700B. The resultant structure 800 may then be subject to further process steps to form a DNA sequencing circuit similar to that described in further detail above.

Figure 9A:
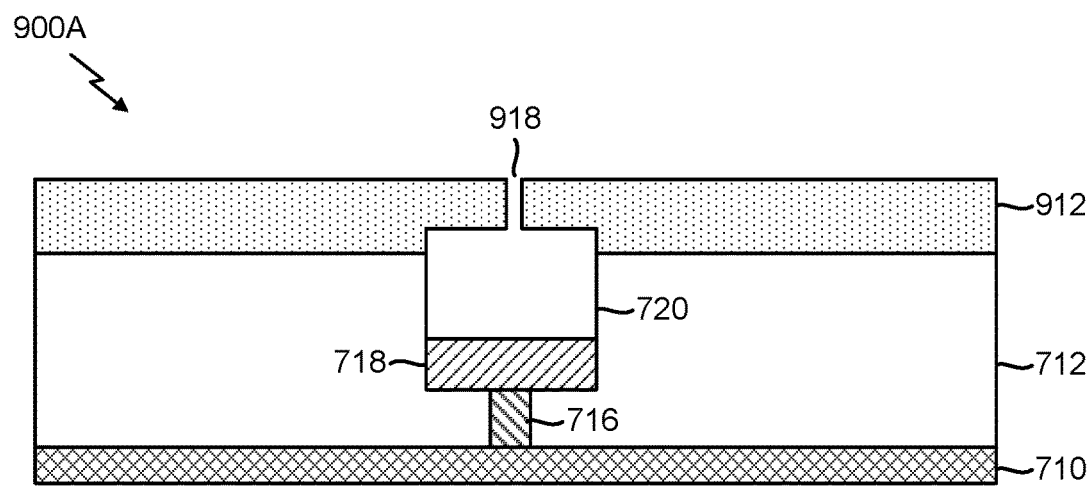
FIG. 9A-9C illustrate an exemplary process flow to form a DNA sequencing circuit from the structure shown in FIG. 8, according to various aspects.
Figure 9B:
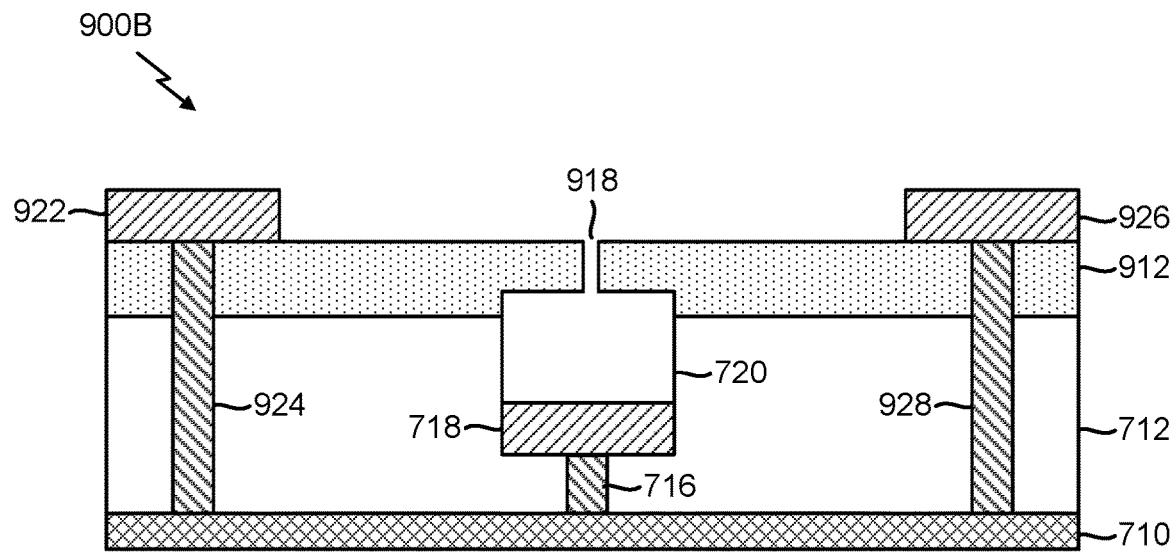
Figure 9C:
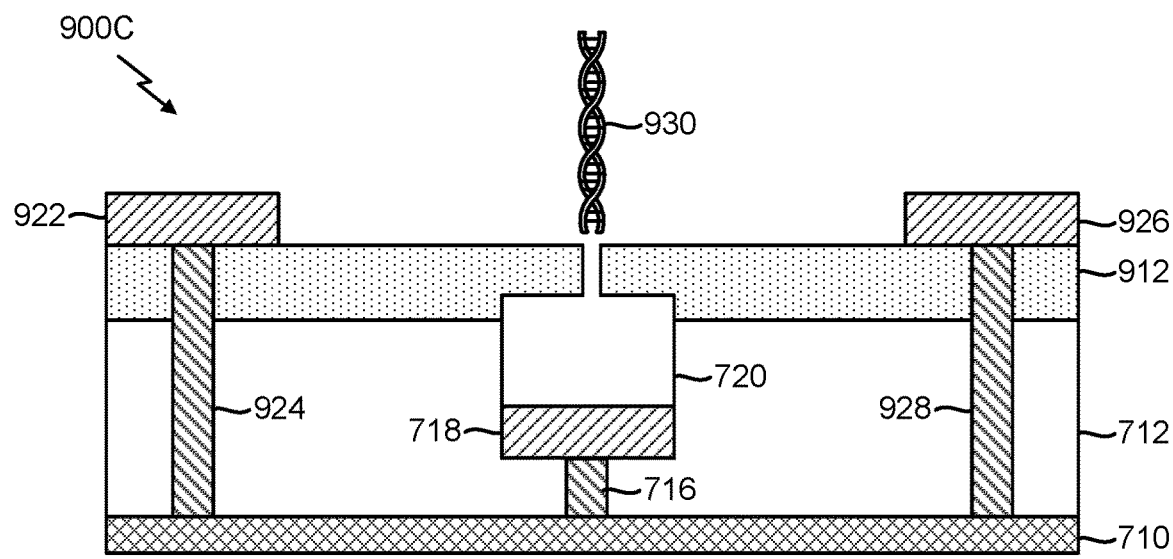

For example, according to various aspects, FIG. 9A-9C illustrate an example process flow to form a DNA sequencing circuit, wherein the process flow shown in FIG. 9A-9C may start from the structure 800 shown in FIG. 8. In particular, FIG. 9A shows a structure 900A in which a chemical mechanical polishing (CMP) process has been performed to remove the Si substrate 610 and planarize the bonded $SiO_2$ layers 612, 714 to form a mechanically robust $SiO_2$ membrane layer 912 having a nanopore 918 formed therein. Referring to FIG. 9B, a second electrode 922, a second interconnect 924, a third electrode 926, and a third interconnect 928 may be formed, resulting in the structure 900B shown therein. For example, in various embodiments, the second and third electrodes 922, 926 may be formed from silver (Ag) and the second and third interconnects 924, 928 may be formed from copper (Cu). However, those skilled in the art will appreciate that other suitable material(s) may be used to form the electrodes 922, 926 and/or the interconnects 924, 928. Furthermore, with reference to FIG. 2, the third electrode 922 may correspond to the common electrode shared among the pair of nanopore-based DNA sensing devices 201, 202. Accordingly, as shown in FIG. 9C, the resultant structure 900B may be substantially similar to the nanopore-based DNA sensing devices 201, 202 shown in FIG. 2, whereby a DNA molecule 930 may pass through the nanopore 918 and changes in electrical current may be measured over time to determine the particular nucleotide sequence in the DNA molecule 930.

Figure 10:
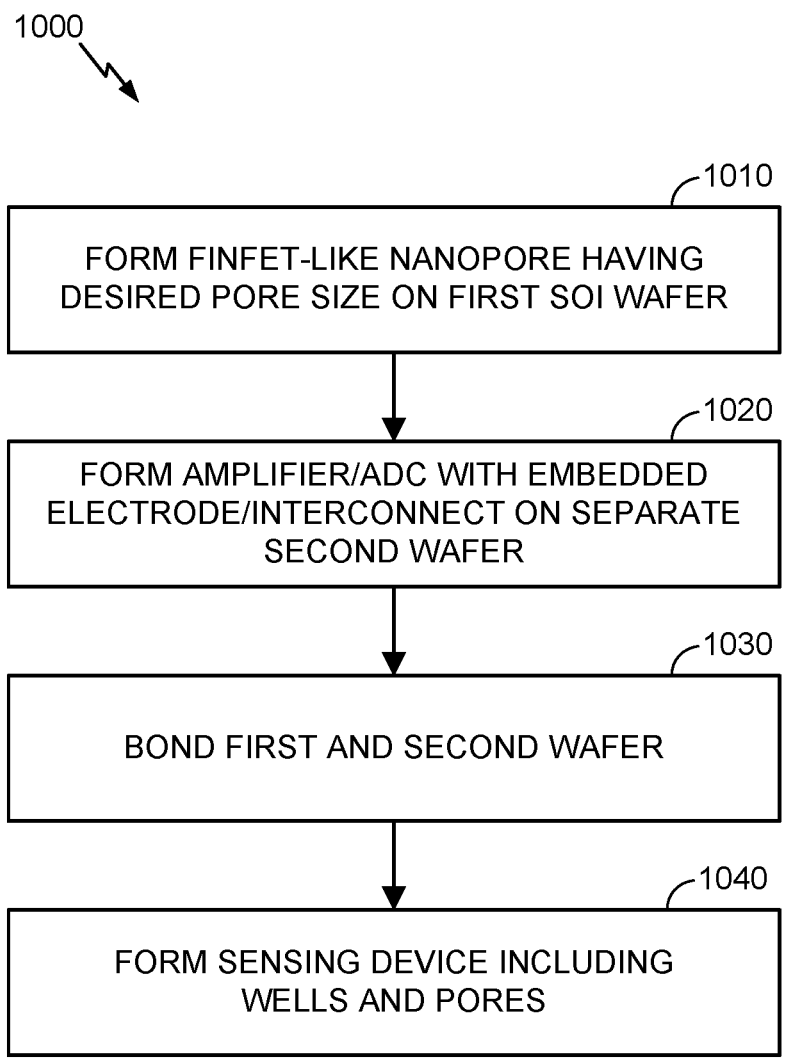
FIG. 10 illustrates an exemplary method to form a DNA sequencing circuit having a silicon-based nanopore with a controllable pore size, a mechanically robust membrane, and a low membrane capacitance, according to various aspects.

According to various aspects, FIG. 10 illustrates an exemplary method 1000 to form a DNA sequencing circuit having a silicon-based nanopore with a controllable pore size, a mechanically robust membrane, and a low membrane capacitance as described above. More particularly, at block 1010, a FinFET-like nanopore having a desired pore size may be formed on a first silicon-on-insulator (SOI) wafer. For example, as described in further detail above with respect to FIG. 6A-6D, a first silicon dioxide ($SiO_2$) layer may be formed on a first silicon (Si) substrate and an Si fin may be formed on the first $SiO_2$ layer, wherein the Si fin may be formed to have a width that corresponds to the desired pore size (e.g., anywhere from approximately one nanometer (1 nm) to one micrometer (1 μm)). The first $SiO_2$ layer may then be grown such that the Si fin is buried therein, and the first $SiO_2$ layer and the buried Si fin may then be planarized through chemical mechanical polishing (CMP). The Si fin may then be removed, for example, dissolved via wet etching in hydrofluoric (HF) acid, resulting in a structure on the first SOI wafer that comprises a FinFET-like nanopore having the desired pore size.

According to various aspects, at block 1020, an amplifier and analog-to-digital converter (ADC) may then be formed with an embedded electrode and interconnect on a (separate) second SOI wafer. For example, as described in further detail above with respect to FIG. 7A-7B, the amplifier and the ADC may form a first layer on the second SOI wafer, a second silicon (Si) substrate may be disposed above the amplifier/ADC layer, and a second $SiO_2$ layer may be formed on the second Si substrate. An opening may then be formed in the second $SiO_2$ layer and the second Si substrate, wherein a first electrode and a first interconnect may be formed in the opening (e.g., from silver (Ag) and copper (Cu)).

According to various aspects, at block 1030, the first SOI wafer and the second SOI wafer may be bonded to one another. In particular, as shown in FIG. 8, the bonding may comprise an $SiO_2$-to-$SiO_2$ bonding between the first $SiO_2$ layer and the second $SiO_2$ layer, wherein the resultant structure may then be subject to further process steps to form a DNA sequencing circuit similar to that described in further detail above.

For example, at block 1040, a chemical mechanical polishing (CMP) process may be performed to remove the first Si substrate and to planarize the bonded $SiO_2$ layers, thereby forming a mechanically robust $SiO_2$ membrane layer with a nanopore formed therein. Additional electrodes and interconnects may then be formed, resulting in a DNA sensing device having the appropriate sensing wells and pores. Accordingly, a DNA molecule may be passed through the nanopore in the formed DNA sensing device and changes in electrical current may be measured over time to determine the particular nucleotide sequence in the DNA molecule.

Those skilled in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those skilled in the art will appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted to depart from the scope of the various aspects and embodiments described herein.

The various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, etc.).

The methods, sequences, and/or algorithms described in connection with the aspects disclosed herein may be embodied directly in hardware, in a software module executed by a processor, or in a combination of the two. A software module may reside in RAM, flash memory, ROM, EPROM, EEPROM, registers, hard disk, a removable disk, a CD-ROM, or any other form of non-transitory computer-readable medium known in the art. An exemplary non-transitory computer-readable medium may be coupled to the processor such that the processor can read information from, and write information to, the non-transitory computer-readable medium. In the alternative, the non-transitory computer-readable medium may be integral to the processor. The processor and the non-transitory computer-readable medium may reside in an ASIC. The ASIC may reside in an IoT device. In the alternative, the processor and the non-transitory computer-readable medium may be discrete components in a user terminal.

In one or more exemplary aspects, the functions described may be implemented in hardware, software, firmware, or any combination thereof. If implemented in software, the functions may be stored on or transmitted over as one or more instructions or code on a non-transitory computer-readable medium. Computer-readable media may include storage media and/or communication media including any non-transitory medium that may facilitate transferring a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, DSL, or wireless technologies such as infrared, radio, and microwave, then the coaxial cable, fiber optic cable, twisted pair, DSL, or wireless technologies such as infrared, radio, and microwave are included in the definition of a medium. The term disk and disc, which may be used interchangeably herein, includes CD, laser disc, optical disc, DVD, floppy disk, and Blu-ray discs, which usually reproduce data magnetically and/or optically with lasers. Combinations of the above should also be included within the scope of computer-readable media.

While the foregoing disclosure shows illustrative aspects and embodiments, those skilled in the art will appreciate that various changes and modifications could be made herein without departing from the scope of the disclosure as defined by the appended claims. Furthermore, in accordance with the various illustrative aspects and embodiments described herein, those skilled in the art will appreciate that the functions, steps, and/or actions in any methods described above and/or recited in any method claims appended hereto need not be performed in any particular order. Further still, to the extent that any elements are described above or recited in the appended claims in a singular form, those skilled in the art will appreciate that singular form(s) contemplate the plural as well unless limitation to the singular form(s) is explicitly stated.

What is claimed is:

1. A deoxyribonucleic acid (DNA) sequencing circuit, comprising:
    a silicon dioxide ($SiO_2$) membrane formed on a surface of a silicon (Si) substrate, the $SiO_2$ membrane having an opening formed therein;
    a second electrode formed on a surface of the $SiO_2$ membrane;
    a first electrode formed in the Si substrate, the first electrode vertically and horizontally spaced from the second electrode without overlapping the second electrode; and
    a sensing device configured to measure changes in an electrical current flowing through the opening between the first electrode and the second electrode over time, wherein the first electrode and the second electrode are formed from silver.

2. The DNA sequencing circuit recited in claim 1, wherein the opening in the $SiO_2$ membrane comprises a nanopore having a pore size in a range from approximately one nanometer (1 nm) to one micrometer (1 μm).

3. The DNA sequencing circuit recited in claim 1, further comprising:
    the sensing device is an amplifier configured to generate a sensing signal indicating the measured changes in the electrical current flowing through the opening over time; and
    an analog-to-digital converter configured to convert the sensing signal to a current waveform indicating a nucleotide sequence in a DNA strand passing through the opening.

4. The DNA sequencing circuit recited in claim 3, wherein the amplifier and the analog-to-digital converter are coupled to the first electrode and the second electrode via a first interconnect and a second interconnect.

5. The DNA sequencing circuit recited in claim 4, wherein the first interconnect and the second interconnect are formed from copper.

6. The DNA sequencing circuit recited in claim 1, further comprising a space divided into a sub-space and an upper sub-space in fluid communication with one another via the opening, wherein the $SiO_2$ membrane is hydrophobic and at least partially separates lower sub-space from the upper sub-space.

7. The DNA sequencing circuit recited in claim 6, wherein the first electrode is in contact with the lower sub-space and the second electrode is in contact with the upper sub-space.

8. The DNA sequencing circuit recited in claim 6, wherein the space is arranged to hold an electrolyte comprising positive ions and negative ions such that a voltage applied to the first electrode and the second electrode causes the electrical current to flow through the opening between the first electrode and the second electrode.

9. The DNA sequencing circuit recited in claim 8, further comprising a voltage source electrically coupled between the first electrode and the second electrode and configured to apply the voltage to the first electrode and the second electrode.

* * * * *